(12) United States Patent
Lualdi

(10) Patent No.: US 11,202,640 B2
(45) Date of Patent: Dec. 21, 2021

(54) MILLING HEAD FOR A MILLING TOOL FOR PROSTHETIC SURGERY OPERATIONS AND CORRESPONDING MILLING TOOL

(71) Applicant: HPF S.R.L., Fagagna (IT)

(72) Inventor: Gabriele Lualdi, Fagagna (IT)

(73) Assignee: HPF S.R.L., Fagagna (IT)

( * ) Notice: Subject to any disclaimer, the term of this patent is extended or adjusted under 35 U.S.C. 154(b) by 0 days.

(21) Appl. No.: 16/802,524

(22) Filed: Feb. 26, 2020

(65) Prior Publication Data

US 2021/0113217 A1    Apr. 22, 2021

(30) Foreign Application Priority Data

Oct. 21, 2019  (IT) .................. 102019000019433

(51) Int. Cl.
*A61B 17/16* (2006.01)

(52) U.S. Cl.
CPC ...... *A61B 17/1617* (2013.01); *A61B 17/1631* (2013.01); *A61B 17/1666* (2013.01); *A61B 17/1684* (2013.01)

(58) Field of Classification Search
CPC . A61B 17/16; A61B 17/1613; A61B 17/1615; A61B 17/1617; A61B 17/1628; A61B 17/1631; A61B 17/1659; A61B 17/1662; A61B 17/1664; A61B 17/1666; A61B 2017/1602
See application file for complete search history.

(56) References Cited

U.S. PATENT DOCUMENTS

| 4,023,572 A * | 5/1977 | Weigand | A61B 17/1666 606/81 |
| 5,709,688 A * | 1/1998 | Salyer | A61B 17/1666 606/81 |
| 8,679,124 B2 * | 3/2014 | Lechot | A61B 17/1617 606/80 |
| 8,784,422 B2 * | 7/2014 | Lechot | A61B 17/1666 606/81 |
| 9,011,442 B2 * | 4/2015 | Victor | A61B 17/1666 606/80 |
| D736,377 S * | 8/2015 | Lualdi | D24/147 |
| 9,107,677 B2 * | 8/2015 | Victor | A61B 17/1668 |
| 9,681,881 B1 * | 6/2017 | Billiet | C04B 35/64 |
| 10,092,304 B2 * | 10/2018 | Fortin | A61B 17/1615 |
| 10,143,480 B2 * | 12/2018 | Victor | A61B 17/1659 |
| 10,485,560 B2 * | 11/2019 | Khalili | A61B 17/1693 |
| 10,512,472 B2 * | 12/2019 | Cameron | A61B 17/1666 |
| 10,543,003 B2 * | 1/2020 | Fortin | A61B 17/1666 |
| 10,682,149 B2 * | 6/2020 | Khalili | A61B 17/164 |
| 10,702,287 B2 * | 7/2020 | Gradel | B21D 35/001 |
| 2006/0189994 A1 * | 8/2006 | Wolford | A61B 17/1617 606/80 |
| 2009/0163921 A1 * | 6/2009 | Lechot | A61B 17/1666 606/81 |

(Continued)

FOREIGN PATENT DOCUMENTS

| EP | 1 764 046 A2 | 3/2007 |
| EP | 2 478 852 A1 | 7/2012 |

*Primary Examiner* — Eric S Gibson
(74) *Attorney, Agent, or Firm* — Marshall, Gerstein & Borun LLP

(57) ABSTRACT

A milling head for a milling tool for prosthetic surgery operations and a milling tool comprising said milling head.

11 Claims, 3 Drawing Sheets

(56) References Cited

U.S. PATENT DOCUMENTS

| | | | |
|---|---|---|---|
| 2012/0191099 A1* | 7/2012 | Victor | A61B 17/1666 606/81 |
| 2016/0089158 A1* | 3/2016 | Fortin | A61B 17/1631 606/81 |
| 2017/0014141 A1* | 1/2017 | Cameron | A61B 17/1617 |
| 2017/0311958 A1* | 11/2017 | Gradel | A61B 17/1666 |
| 2017/0354424 A1* | 12/2017 | Khalili | A61B 17/1693 |
| 2019/0083110 A1* | 3/2019 | Wozencroft | A61B 17/1666 |
| 2020/0015829 A1* | 1/2020 | Khalili | A61B 17/162 |

\* cited by examiner

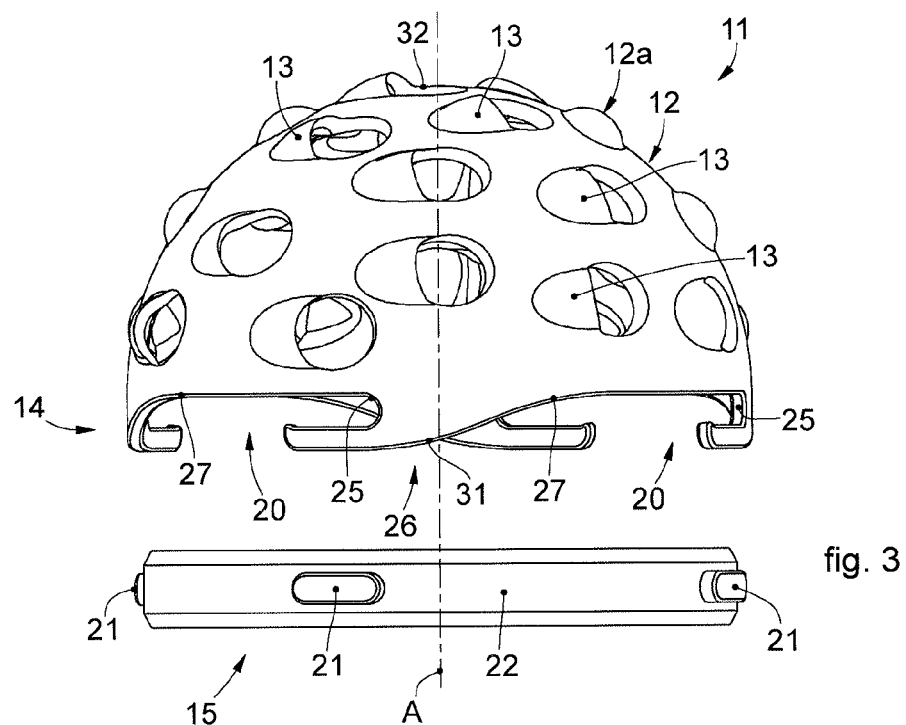
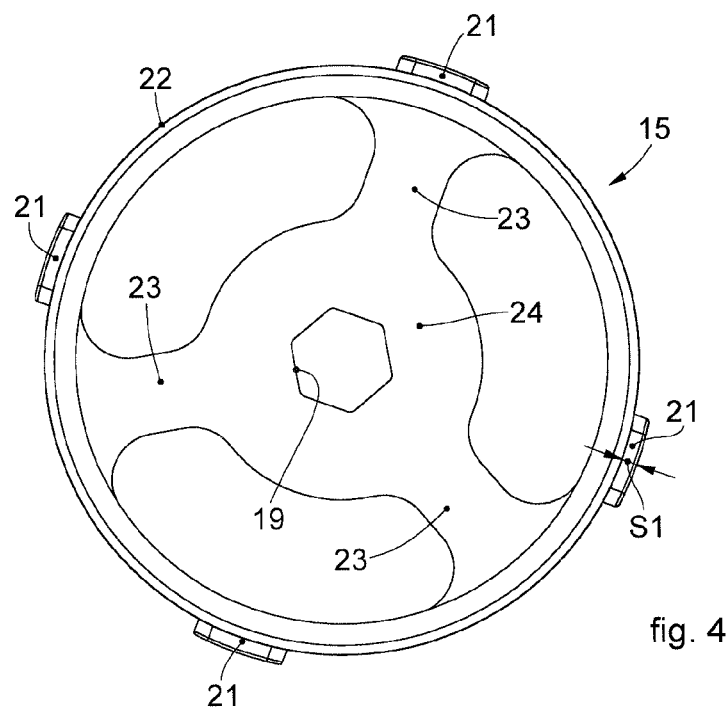

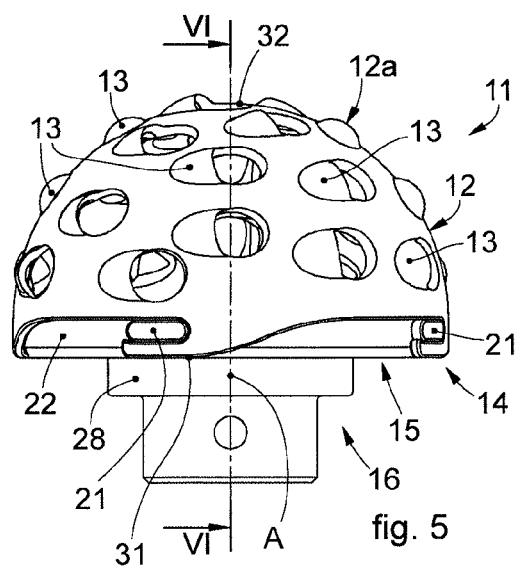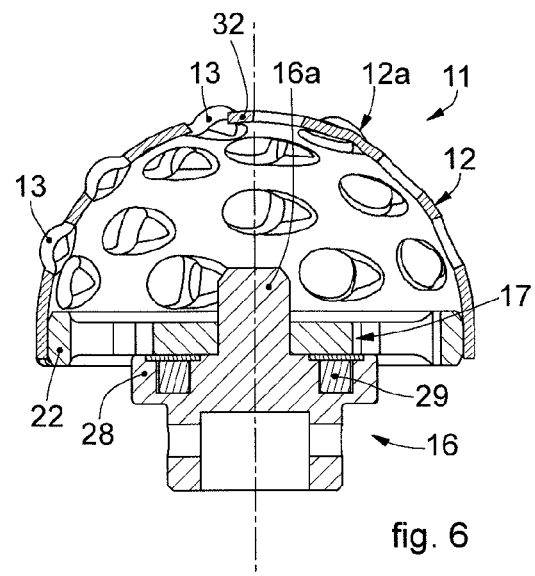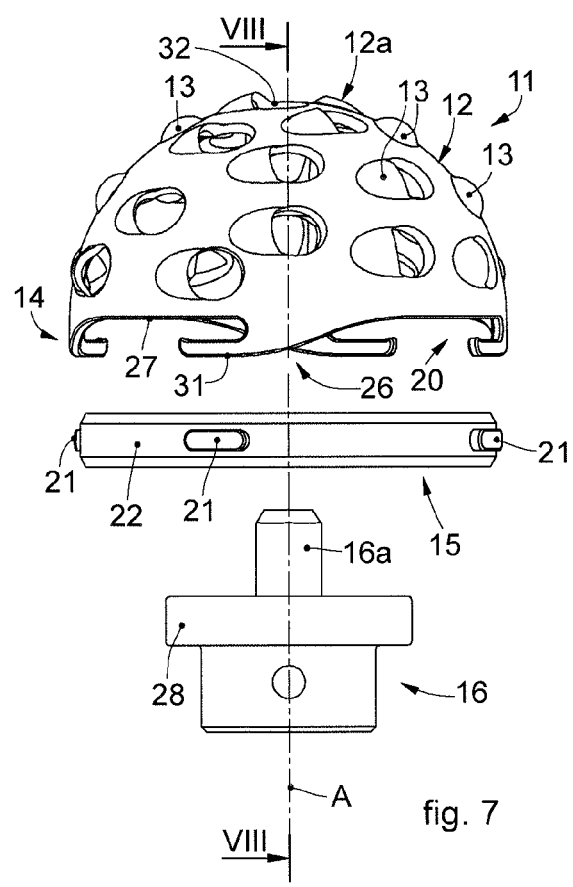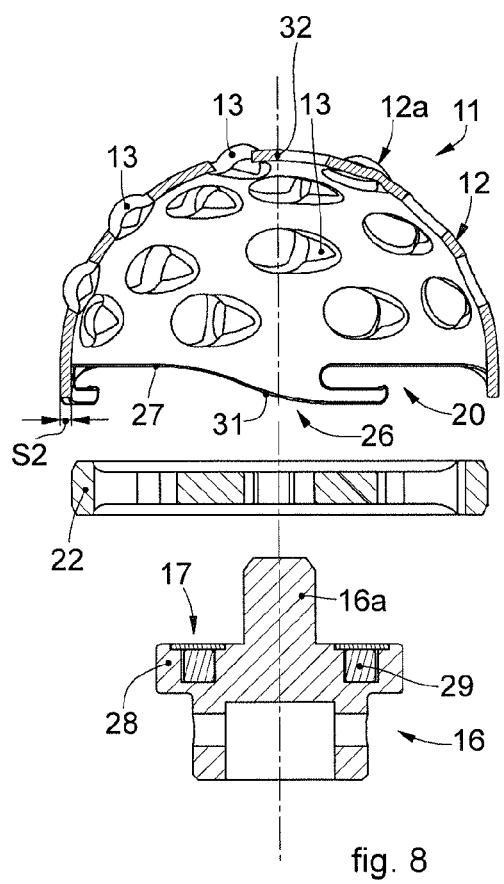

MILLING HEAD FOR A MILLING TOOL FOR PROSTHETIC SURGERY OPERATIONS AND CORRESPONDING MILLING TOOL

FIELD OF THE INVENTION

The present invention concerns a milling head for a milling tool for prosthetic surgery operations, usable for example to make a bone seating, for example to install an acetabular hip prosthesis, or a shoulder prosthesis or other, able to be associated with a corresponding manipulator device.

The present invention also concerns a milling tool equipped with the milling head as above.

BACKGROUND OF THE INVENTION

In general, milling tools are known that can be used during prosthetic surgery operations and are conformed to make coordinated and mating bone seatings suitable for the disposition and implantation of corresponding components of surgical prostheses.

In particular, milling tools are known that can be used to make the hemispherical seatings, or in any case seatings with a spherical cap, suitable for the installation of coordinated acetabular cups of the hip prostheses.

These known milling tools generally provide an internally hollow milling head, with sizes correlated to the bone seating to be made and on which a plurality of through apertures are made, provided with cutting and protruding edges, to perform a mechanical excavation action on the bone.

In this way, rotating about an axis of rotation, or of milling, and performing a mechanical removal action of the bone material, this type of milling tools create an impression on the bone of desired size and conformation, substantially corresponding to the shape of the milling head.

It is known that the milling tools as above are operatively associated with manipulator devices, which can be both of the manual and also of the automatic type.

In particular, the manipulator devices can be associated with an attachment part stably fixed to the base of the milling head as above, with an anchoring function for the manipulator device and for the transmission of the torque.

It is also known that these milling tools have to be subjected to washing and sterilization operations after each operation, including through the use of washing and sterilization machines designed for this purpose.

These washing and sterilization operations naturally entail an increase in the overall costs deriving from the use of these known tools or utensils.

Documents EP-A-2.478.852, US-A-2016/0089158 and EP-A-1.764.046 describe milling tools for orthopedic surgery, in particular for prosthetic surgery, of a known type.

Other limitations and disadvantages of conventional solutions and technologies will be clear to a person of skill after reading the remaining part of the present description with reference to the drawings and the description of the embodiments that follow, although it is clear that the description of the state of the art connected to the present description must not be considered an admission that what is described here is already known from the state of the prior art.

There is therefore a need to perfect a milling tool for prosthetic surgery operations which can overcome at least one of the disadvantages of the state of the art.

One purpose of the present invention is therefore to provide a milling tool for prosthetic surgery operations which allows to drastically reduce the risk of contamination by external agents, such as viruses, bacteria or suchlike, thus allowing to reduce the risks of contamination for a patient.

It is also a purpose of the present invention to provide a milling tool which allows to limit further washing and sterilization operations, to be carried out possibly only on determinate zones or parts of the milling tool, thereby optimizing the washing and sterilization operations, and possibly even eliminating them at least for the operative cutting parts of the milling tool.

Another purpose of the present invention is to provide a milling tool for prosthetic surgery operations which is simple and compact in shape, thus allowing production and supply at lower costs compared to what occurs with known milling tools.

Another purpose of the invention is to provide a milling tool which is simple, effective and which allows to perform the milling operations for which it is intended in an optimal and precise manner.

The Applicant has devised, tested and embodied the present invention to overcome the shortcomings of the state of the art and to obtain these and other purposes and advantages.

SUMMARY OF THE INVENTION

The present invention is set forth and characterized in the independent claims. The dependent claims describe other characteristics of the invention or variants to the main inventive idea.

In accordance with some embodiments, a milling head for a milling tool for prosthetic surgery operations is made of metal and has a base perimeter edge.

The milling head is provided with an external cutting part which has a milling surface from which a plurality of protruding cutting elements project, and a coupling part defined along the base perimeter edge as above and provided with a plurality of recessed coupling seatings, circumferentially present along the base perimeter edge.

In accordance with some embodiments, a milling tool is provided comprising the milling head as above and an attachment part connected in a selectively releasable manner to the milling head in correspondence with the coupling part of the milling head.

The coupling part has a discoidal shape and comprises a peripheral band with a continuous annular shape provided with a plurality of holding elements projecting from the peripheral band in a radial direction toward the outside.

The recessed coupling seating is configured to determine a releasable bayonet-type connection between the milling head and the attachment part.

Each recessed coupling seating is provided with a lead-in portion which allows access to any one of the holding elements whatsoever, and with an end-of-travel portion configured to receive a respective holding element constraining, to each other and in a releasable manner, the milling head and the attachment part at least in the axial direction.

BRIEF DESCRIPTION OF THE DRAWINGS

These and other characteristics of the present invention will become apparent from the following description of some embodiments, given as a non-restrictive example with reference to the attached drawings wherein:

FIG. 3 is a lateral view of FIG. 2;

FIG. 4 is a bottom plan view of a component of FIG. 3;

FIG. 5 is a lateral view of a milling tool in accordance with embodiments described here;

FIG. 6 is a section along line VI-VI of FIG. 5;

FIG. 7 is a lateral view with separated parts of the milling tool of FIG. 5;

FIG. 8 is a section along line VIII-VIII of FIG. 7.

To facilitate comprehension, the same reference numbers have been used, where possible, to identify identical common elements in the drawings. It is understood that elements and characteristics of one embodiment can conveniently be incorporated into other embodiments without further clarifications.

DESCRIPTION OF EMBODIMENTS

Figure 1:
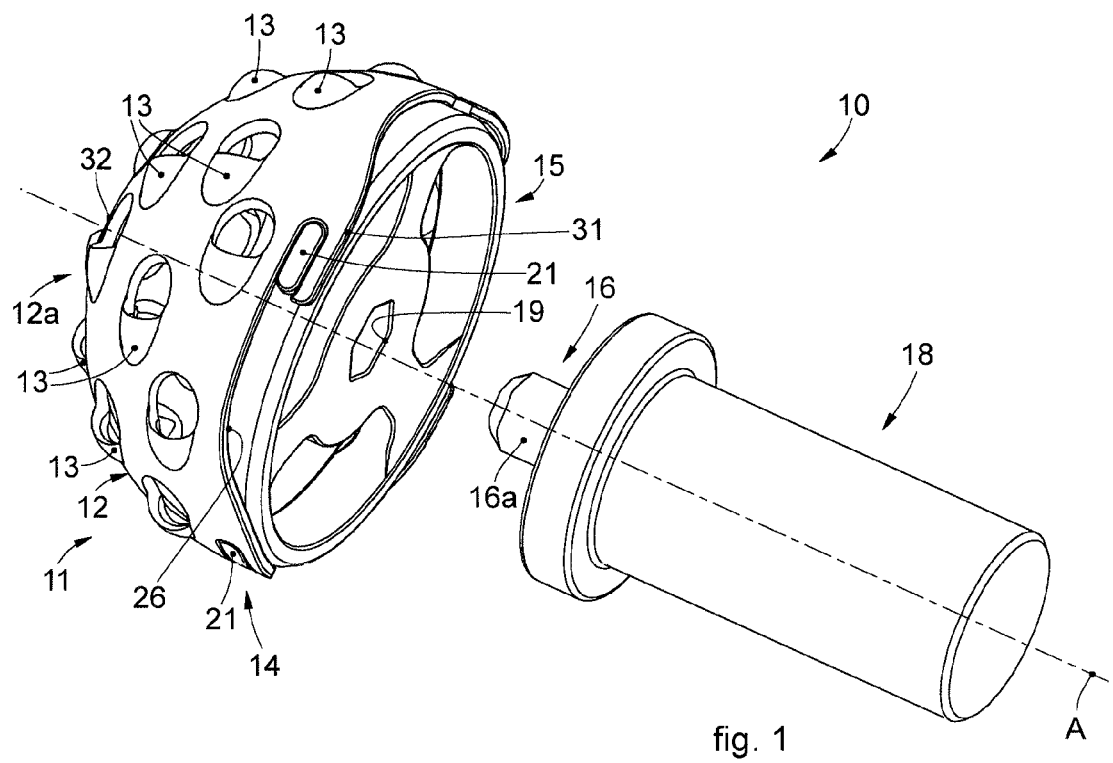
FIG. 1 is a three-dimensional view of a milling tool in accordance with embodiments described here.

We will now refer in detail to the possible embodiments of the invention, of which one or more examples are shown in the attached drawings. Each example is supplied by way of illustration of the invention and shall not be understood as a limitation thereof. For example, one or more characteristics shown or described insomuch as they are part of one embodiment can be varied or adopted on, or in association with, other embodiments to produce other embodiments. It is understood that the present invention shall include all such modifications and variants.

Before describing these embodiments, we must also clarify that the present description is not limited in its application to details of the construction and disposition of the components as described in the following description using the attached drawings. The present description can provide other embodiments and can be obtained or executed in various other ways. We must also clarify that the phraseology and terminology used here is for the purposes of description only, and cannot be considered as limitative.

Embodiments described using the attached drawings concern a milling head 11 for a milling tool 10 for prosthetic surgery operations, in particular to make concave seatings for the implantation of prostheses, for example of the shoulder or hip, and also concern the milling tool 10 provided with the milling head 11.

In accordance with some embodiments, the milling head 11 is made of metal and has a base perimeter edge 31.

The milling head can have the shape of a cap, in particular hemispherical, or other suitable shapes, advantageously axisymmetric, such as for example a cylindrical shape, or other shapes suitable to make concave seatings for the implantation of a prosthesis.

The milling head 11 is provided with an external cutting part 12 which has a milling surface 12a from which a plurality of protruding cutting elements 13 project.

The milling head 11 is also provided with a coupling part 14 defined along the base perimeter edge 31 and provided with a plurality of recessed coupling seatings 20 circumferentially present along the base perimeter edge 31.

In accordance with some embodiments, the recessed coupling seatings 20 are disposed angularly distanced with a regular pitch on the coupling part 14.

According to possible embodiments, advantageously, the number of recessed coupling seatings 20 is at least two, in which case the recessed coupling seatings 20 are positioned in a diametrically opposite manner.

In accordance with other possible embodiments, the milling head 11 can comprise three recessed coupling seatings 20 disposed at 120° from each other.

In accordance with some embodiments, the milling head 11 can comprise four recessed coupling seatings 20 disposed at 90° from each other.

In accordance with some embodiments, the recessed coupling seatings 20 are open in a direction orthogonal to an operative axis A of symmetry for the milling head 11, that is, they are through, orthogonally, toward the inside of the milling head 11.

In accordance with some embodiments, each of the recessed coupling seatings 20 comprises a lead-in portion 27 and an end-of-travel portion 25, disposed circumferentially downstream with respect to the respective lead-in portion 27.

The lead-in portion 27 is open in a direction parallel to the operative axis A, and the end-of-travel portion 25 is open in a circumferential direction only toward the respective lead-in portion 27.

The recessed coupling seating 20 is configured to determine a releasable bayonet-type connection, in which the lead-in portion 27 allows access for a holding element and the end-of-travel portion 25 is configured to receive the holding element determining a constraint thereof at least in the direction of the operative axis A, as will be better described below with reference to the milling tool 10.

In accordance with some embodiments, the base perimeter edge 31 defines an end aperture 26 having a circular shape and having a circumferential extension greater than the circumferential extension of each of the recessed coupling seatings 20.

In accordance with some embodiments, the milling head can be disposable, or it can be reused after appropriate sterilization.

In accordance with some embodiments, the cutting elements 13 of the external cutting part 12, preferably, can be distributed uniformly on the milling surface 12a, and through apertures are made in correspondence therewith for the discharge of the material removed.

The cutting elements 13 can have various shapes and have the function of cutting or milling the bone component, while the through apertures allow the bone residues to be removed from the cutting or milling zone.

According to a possible solution, the cutting elements 13 defined above are made in the thickness of the milling head 11 and are each provided with at least one cutting edge to allow the removal of the material.

In accordance with possible embodiments, at least the cutting part 12 is made of titanium.

Advantageously, the milling head 11 can be entirely made of titanium since it is hypoallergenic and biocompatible.

In accordance with some embodiments, the milling tool 10 comprises a milling head 11.

The milling tool 10 also comprises an attachment part 15 connected in a selectively releasable manner to the milling head 11 in correspondence with the coupling part 14.

The milling tool 10 comprises an attachment head 16 provided with clamping means 17 which can be selectively activated for a stable and releasable connection to the attachment part 15, said attachment head 16 being able to be connected to a manipulator device 18.

The attachment part 15 is provided with a central connection seating 19 having a polygonal shape to allow a selectively releasable connection with the attachment head 16.

In accordance with some embodiments, the attachment part 15 has a discoidal shape and comprises a peripheral band 22 with a continuous annular shape provided with a plurality of holding elements 21 configured to engage, each one, a respective one of said recessed coupling seatings 20 of the coupling part 14 of the milling head 11.

In accordance with some embodiments, the base perimeter edge 31 defines the end aperture 26 having a circular shape in which the attachment part 15 is connected in a removable manner.

In accordance with some embodiments, the milling head 11 and the attachment part 15 are made in a separate body and are selectively connected to each other in a removable manner immediately before the surgical operation, for example during the preparation of the milling tool 10.

The attachment part 15 can be disposable or it can be reused after appropriate sterilization.

If it is reusable, the attachment part 15 is therefore, to all effects, a component of the surgical instruments.

The possibility of separating the milling head 11 from the attachment part 15 allows to significantly simplify the sterilization operations of the milling tool 10.

In particular, the internal zone defined by the milling head 11 and by the attachment part 15 is the zone where the organic waste generated by the milling operation mostly collects. The possibility of having complete access to the internal zone as above by removing the attachment part 15 simplifies the sterilization operations and reduces the time required for them.

Furthermore, the absence of fixing means such as screws, pins, bolts or other, limits the number of components considerably simplifying and speeding up the assembly and disassembly operations of the attachment part 15 onto/from the milling head 11.

The attachment part 15, at least in an operative condition, is aligned with the milling head 11 along the operative axis A, which in this case is through both through the center of the connection seating 19 and also through the center of the milling head 11, orthogonally to the aperture 26.

The operative axis A is therefore an axis of symmetry for the milling head 11 and for the attachment part 15.

The attachment part 15 has a transverse size, that is, orthogonal to the operative axis A, slightly smaller than the size of the aperture 26. In this way, the attachment part 15 can be inserted into the aperture 26.

In particular, the peripheral band 22 of the attachment part 15 has an external diameter substantially equal to, or slightly smaller than, the internal diameter of the aperture 26. In this way, the peripheral band 22 can substantially come into sliding contact with the internal surface of the coupling part 14.

The peripheral band 22 of the attachment part 15 can be positioned in part of the cavity defined by the milling head 11, that is, it can be at least partly recessed in it. This positioning of the attachment part 15 allows to obtain an increase in the containing rigidity of the milling head 11, preventing its collapse in correspondence with the coupling part 14, made particularly lighter by the presence of the recessed coupling seatings 20.

In accordance with some embodiments, the holding elements 21 can be projecting from the peripheral band 22 in a radial direction toward the outside, that is, in the opposite direction with respect to the connection seating 19 disposed in a central position.

The holding elements 21 can be disposed angularly distanced with a regular pitch on the peripheral band 22, so as to correspond, at least in the operative condition, to the recessed coupling seatings 20.

The number of holding elements 21 is correlated to the number of recessed coupling seatings 20.

In accordance with some embodiments, the shape of the recessed coupling seating 20 is mating with the shape of the holding element 21. For example, the holding elements 21 can have the shape of a parallelepiped, a cylinder or portions thereof, and the corresponding recessed coupling seatings 20 can have a rectangular, semicircular, or other suitable mating shape.

Evidently, it is advantageous for the coupling between the holding element 21 and the respective recessed coupling seating 20 to be rather precise, so as to avoid unwanted vibrations and guarantee an optimal transfer of the torque.

In accordance with some embodiments, the attachment part 15 also comprises spokes, or arms, 23 substantially equally distanced angularly and converging in a central hub 24 where the central connection seating 19 is present.

Figure 2:
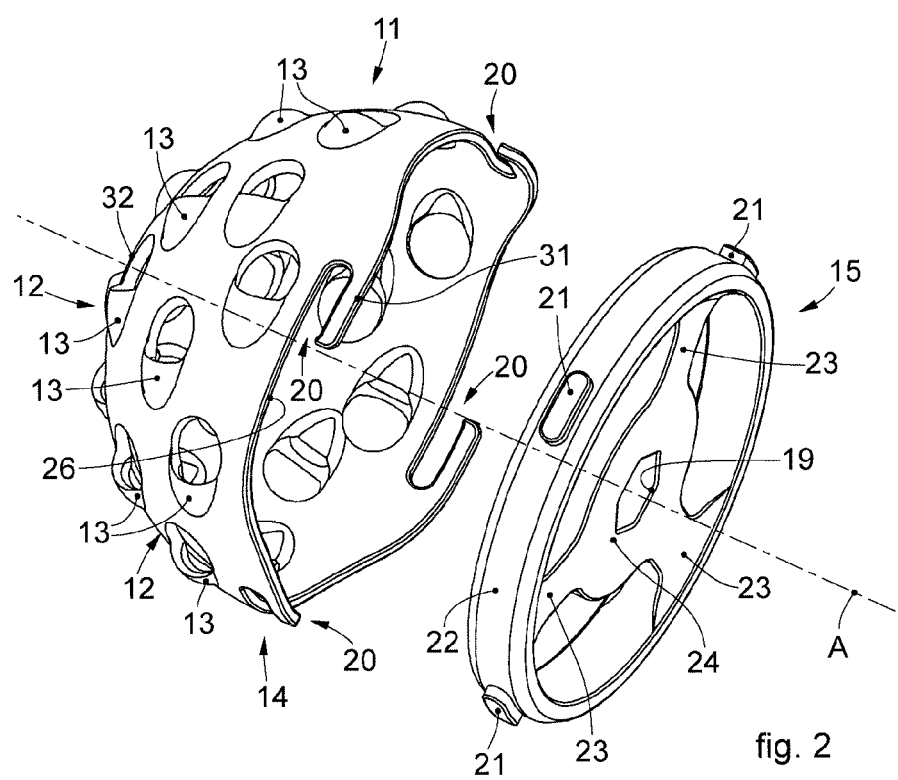
FIG. 2 is a three-dimensional and exploded view of two components of FIG. 1.

According to some embodiments, shown in FIGS. 1-2 and FIG. 4, the attachment part 15 can comprise three spokes 23 equally distanced angularly by about 120°.

In possible further embodiments, the attachment part 15 can be formed by a bar, or crosspiece, provided with the central connection seating 19 and defining only two diametrically opposite spokes, or arms, 23.

In accordance with some embodiments, each recessed coupling seating 20 comprises the lead-in portion 27 configured to allow the sliding of a respective holding element 21, and the end-of-travel portion 25 configured to clamp the holding element 21 into position.

The end-of-travel portion 25 is disposed circumferentially downstream with respect to the lead-in portion 27. The terms "downstream" and "upstream" define a spatial circumferential reference with respect to a rotation of the milling head in a clockwise direction.

The lead-in portion 27 is positioned before the end-of-travel portion 25 of a respective recessed coupling seating 20, which constitutes a natural extension thereof.

The lead-in portion 27 is open in a direction parallel to the operative axis A so that when the attachment part 15 is associated with the milling head 11, the attachment part 15 can rest on the lead-in portion 27.

In particular, when the attachment part 15 enters the aperture 26, the holding elements 21 rest on the lead-in portion 27. In the event there is no suitable initial alignment, it is sufficient to slightly rotate the attachment part 15 in a clockwise direction with respect to the milling head 11 so that the holding elements 21 engage respective recessed coupling seatings 20 in correspondence with respective lead-in portions 27.

The end-of-travel portion 25 is defined by a recess made directly in the coupling part 14.

The end-of-travel portion 25 is open in the direction of the lead-in portion 27 so as to allow the entry of a respective holding element 21 of the attachment part 15.

In accordance with some embodiments, the recessed coupling seating 20 is configured to determine a releasable bayonet-type connection between the milling head 11 and the attachment part 15, in which each lead-in portion 27 allows access to any one of said holding elements 21 and the end-of-travel portions 25 are configured to receive respective ones of said holding elements 21 constraining, to each other and in a releasable manner, the milling head 11 and the attachment part 15 at least in the axial direction, that is, the direction of the operative axis A.

The end-of-travel portion 25 is closed in the direction opposite the lead-in portion 27 allowing to clamp in position the attachment part 15, at least in the direction of the operative axis A and with respect to a rotation in a clockwise direction with respect to the operative axis A.

In this way, the attachment part 15 is, at least temporarily, integral with the milling head 11.

Another clockwise rotation of the attachment part 15 causes the complete rotation of the milling head 11.

In particular, during use, the milling head 11 is made to rotate by means of the attachment head 16 in a clockwise direction and the end-of-travel portion 25, as well as allowing the transmission of the torque, also acts as a safety system preventing the milling head 11 from being decoupled from the attachment part 15.

At the end of the milling operation, it is possible to decouple the milling head 11 from the attachment part 15 by simply rotating the attachment part 15 in an anti-clockwise direction, since no other constraints are present.

In accordance with some embodiments, the end-of-travel portion 25 has a shape mating with the shape of the holding element 21.

In particular, the sizes of the end-of-travel portion 25 are slightly larger, but not much larger, than the holding element 21, so as to define a clearance sufficiently narrow to allow the circumferential coupling with the holding element 21, preventing vibrations during use.

The holding elements 21 have a radial thickness S1 correlated to a radial thickness S2 of the milling head 11.

In particular, the radial thickness S1 of the holding elements 21 is equal to the radial thickness S2 of the milling head 11.

In this way, the connection between the attachment part 15 and the milling head 11 is stable and secure. Furthermore, the holding elements 21 are not radially protruding from the recessed coupling seatings 20, but remain advantageously confined therein.

In possible implementations, the milling head 11 has a radial thickness S2 comprised between 0.8 mm and 1.2 mm.

In other possible implementations, the holding elements 21 have a radial thickness S1 comprised between 0.8 mm and 1.2 mm.

In accordance with some embodiments, by aligning the attachment part 15 with the milling head 11 with respect to the operative axis A and resting it on the latter in correspondence with the coupling part 14, it is sufficient to rotate the attachment part 15 about the operative axis A in a clockwise direction until the holding elements 21 engage respective recessed coupling seatings 20. Each holding element 21 rests on the lead-in portion 27 of the respective recessed coupling seating 20 sliding along it, until it ends its travel in the end-of-travel portion 25.

Since the lead-in portion 27 is inclined with respect to the operative axis A at least in a first part thereof, the rotation of the attachment part 15, while it slides on the lead-in portion 27, determines a translation thereof in the direction of the operative axis A and an insertion thereof in the aperture 26 in a gradual manner.

According to some embodiments, the attachment part 15 can be at least partly made of titanium.

Advantageously, the milling tool 10 can be entirely made of titanium.

Titanium is particularly advantageous since it is hypoallergenic and biocompatible.

Alternatively, one, several or all of the components as above can be made of steel. For example, the central hub 24 of the attachment part 15 where the central connection seating 19 is present can be made of steel, so as to allow a possible fixing, of the magnetic type, to respective clamping means 17.

In possible embodiments, the attachment head 16 has a polygonal section shape, for example quadrangular or hexagonal (FIG. 1 and FIGS. 6-8) mating with the shape of the connection seating 19.

The polygonal, in particular the hexagonal, shape of the central connection seating 19 is advantageous for an effective transmission of the torque required for the rotation of the milling tool 10 in question.

In particular, the attachment head 16 is provided with a connection portion 16a projecting from the protruding annular ring 28 and having the hexagonal section shape as above.

The hexagonal shape of the central connection seating 19 and of the attachment head 16 allows to distribute the connection force between the attachment head 16 and the attachment part 15 in a more homogeneous manner. With the same transmitted force, the hexagonal shape allows to reduce the size of the connection seating 19. This attachment head 16 can be provided for the connection to a manipulator device 18.

In possible embodiments described using FIG. 1 and FIGS. 5-8, the attachment head 16 is provided with a protruding annular ring 28 for abutment against the attachment part 15 (see for example FIGS. 5-8). The provision of the protruding annular ring 28 is advantageous, since it defines an end-of-travel or a safety abutment for the connection between the attachment head 16 and the attachment part 15, also preventing the rise of situations in which, by applying a thrust and pressure on the manipulator device 18, the attachment head 16 is thrust excessively and in an undesired manner beyond the attachment part 15, toward the inside of the milling head 11, with the evident risks this situation entails.

In accordance with some embodiments, the clamping means 17 of the attachment head 16 comprise a magnetic element 29 configured to selectively abut with the attachment part 15 in correspondence with the connection seating 19.

In accordance with some embodiments, shown in FIG. 6 and FIG. 8, the attachment head 16 is provided with a groove 30, made on the protruding annular ring 28 and circumscribed to the connection portion 16a, in which the magnetic element 29 is positioned.

The magnetic element 29 has an annular shape, substantially mating with the shape of the groove 30.

Advantageously, the presence of the magnetic element 29 allows to transmit a uniform connection force onto the attachment part 15. In fact, the annular shape of the magnetic element 29 allows to act on the whole perimeter zone around the connection seating 19.

In accordance with possible embodiments, the clamping means 17 are provided with an elastic retractable element configured to selectively engage the attachment part 15 in correspondence with the connection seating 19.

The elastic retractable element, therefore, acts as an advantageous selective clamping element with the attachment part 15. This is favorably useful, for example, to prevent undesired slippage or uncoupling between the attachment part 15 and the attachment head 16 associated with the manipulator device 18.

It is clear that modifications and/or additions of parts may be made to the milling tool for prosthetic surgery operations as described heretofore, without departing from the field and scope of the present invention.

It is also clear that, although the present invention has been described with reference to some specific examples, a person of skill in the art shall certainly be able to achieve many other equivalent forms of a milling tool for prosthetic surgery operations, having the characteristics as set forth in the claims and hence all coming within the field of protection defined thereby.

In the following claims, the sole purpose of the references in brackets is to facilitate reading: they must not be considered as restrictive factors with regard to the field of protection claimed in the specific claims.

The invention claimed is:

1. A milling tool for prosthetic surgery operations, comprising:
a milling head made of metal, the milling head having a base perimeter edge, the milling head being provided with an external cutting part having a milling surface from which a plurality of protruding cutting elements project, and including a coupling part defined along the base perimeter edge and provided with a plurality of recessed coupling seatings circumferentially present along the base perimeter edge;
wherein said tool also comprises:
an attachment part connected in a selectively releasable manner to said milling head in correspondence with the coupling part of said milling head,
an attachment head provided with clamping means selectively activatable for a stable and releasable connection to said attachment part, said attachment head being able to be connected to a manipulator device,
said attachment part being provided with a central connection seating, having a polygonal shape, in order to allow a selectively releasable connection with said attachment head.

2. The milling tool as in claim 1, wherein the plurality of recessed coupling seatings are disposed angularly distanced with a regular pitch on said coupling part, wherein each of said recessed coupling seatings comprises a lead-in portion and an end-of-travel portion disposed circumferentially downstream with respect thereto.

3. The milling tool as in claim 2, wherein said recessed coupling seatings are open in a direction orthogonal to an operative axis of symmetry for said milling head.

4. The milling tool as in claim 2, wherein said lead-in portion is open in a direction parallel to said operative axis, and said end-of-travel portion is open in a circumferential direction only toward said lead-in portion.

5. The milling tool as in claim 1, wherein said attachment part has a discoidal shape and comprises a peripheral band with a continuous annular shape provided with a plurality of holding elements projecting from said peripheral band in a radially outward direction relative to an operative axis.

6. The milling tool as in claim 5, wherein said holding elements are disposed angularly distanced with a regular pitch on said peripheral band.

7. The milling tool as in claim 5, wherein said plurality of recessed coupling seatings are configured to determine a releasable bayonet-type connection between said milling head and said attachment part, wherein the plurality of recessed coupling seatings are disposed angularly distanced with a regular pitch on said coupling part, and wherein each of said recessed coupling seatings comprises a lead-in portion and an end-of-travel portion disposed circumferentially downstream with respect thereto, wherein each lead-in portion allows access to any one of said holding elements, and wherein said end-of-travel portions are configured to receive respective ones of said holding elements constraining, to each other and in a releasable manner, said milling head and said attachment part at least in the axial direction.

8. The milling tool as in claim 7, wherein said end-of-travel portion has a shape mating with a shape of said holding elements.

9. The milling tool as in claim 5, wherein said holding elements have a radial thickness substantially equal to a radial thickness of said milling head.

10. The milling tool as in claim 1, wherein said attachment part is made of titanium.

11. The milling tool as in claim 1, wherein said milling tool is entirely made of titanium.

* * * * *